US 7,692,147 B2
Apr. 6, 2010

(12) United States Patent
Hu et al.

(54) REAL-TIME, CONTINUOUS-WAVE TERAHERTZ IMAGING USING A MICROBOLOMETER FOCAL-PLANE ARRAY

(75) Inventors: Qing Hu, Wellesley, MA (US); Alan W. Min Lee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 321 days.

(21) Appl. No.: 11/385,039

(22) Filed: Mar. 20, 2006

(65) Prior Publication Data

US 2008/0156991 A1 Jul. 3, 2008

Related U.S. Application Data

(60) Provisional application No. 60/663,902, filed on Mar. 21, 2005.

(51) Int. Cl.
*G01N 21/35* (2006.01)

(52) U.S. Cl. .................................. 250/336.1

(58) Field of Classification Search ................ 250/250, 250/336.1, 336.2, 338.1, 339.06, 339.11, 250/341.1, 341.8
See application file for complete search history.

(56) References Cited

U.S. PATENT DOCUMENTS

| | | | |
|---|---|---|---|
| 5,528,035 A | 6/1996 | Masarik et al. | |
| 6,242,740 B1 * | 6/2001 | Luukanen et al. | 250/353 |
| 6,404,397 B1 * | 6/2002 | Grinberg et al. | 343/753 |
| 6,441,368 B1 * | 8/2002 | Grinberg et al. | 250/239 |
| 6,777,684 B1 * | 8/2004 | Volkov et al. | 250/341.1 |
| 2003/0222217 A1 * | 12/2003 | Luukanen | 250/336.2 |
| 2004/0155665 A1 | 8/2004 | Arnone et al. | |
| 2006/0058196 A1 * | 3/2006 | Yefremenko et al. | 505/190 |
| 2006/0219922 A1 * | 10/2006 | Watanabe et al. | 250/341.8 |
| 2006/0231762 A1 * | 10/2006 | Ohtake et al. | 250/341.8 |
| 2006/0255277 A1 * | 11/2006 | Cole et al. | 250/341.1 |
| 2007/0228280 A1 * | 10/2007 | Mueller | 250/341.1 |
| 2007/0235658 A1 * | 10/2007 | Zimdars et al. | 250/390.07 |

FOREIGN PATENT DOCUMENTS

EP 0 903 566 3/1999

OTHER PUBLICATIONS

P.L. Richards, Bolometers for Infrared and millimeter waves, Jul. 1, 1994, J. Appl. Phys. 76 (1), pp. 1-24.*
S. Wang et al., Tomographic imaging with a terahertz binary lens, Mar. 24, 2003, Applied Physics Letters vol. 82, No. 12, pp. 1821-1823.*

* cited by examiner

*Primary Examiner*—David P Porta
*Assistant Examiner*—Djura Malevic
(74) *Attorney, Agent, or Firm*—Thomas J. Engellenner; Reza Mollaaghababa; Nutter McClennen & Fish LLP

(57) ABSTRACT

The present invention generally provides a terahertz (THz) imaging system that includes a source for generating radiation (e.g., a quantum cascade laser) having one or more frequencies in a range of about 0.1 THz to about 10 THz, and a two-dimensional detector array comprising a plurality of radiation detecting elements that are capable of detecting radiation in that frequency range. An optical system directs radiation from the source to an object to be imaged. The detector array detects at least a portion of the radiation transmitted through the object (or reflected by the object) so as to form a THz image of that object.

36 Claims, 9 Drawing Sheets

REAL-TIME, CONTINUOUS-WAVE TERAHERTZ IMAGING USING A MICROBOLOMETER FOCAL-PLANE ARRAY

RELATED APPLICATION

The present application claims priority to a provisional application entitled "Real-time, Continuous-wave Terahertz Imaging Using a Microbolometer Focal-Plane Array," filed on Mar. 21, 2005 and having a Ser. No. 60/663,902, which is herein incorporated by reference.

FEDERALLY SPONSORED RESEARCH

The invention was made with government support under Grant Number ECS-0217782, awarded by NSF, Grant Number NNG04GC11G, awarded by NASA, and Grant Number F49620-00-1-0331, awarded by Air Force Aerospace Research. The Government has certain rights in the invention.

BACKGROUND OF THE INVENTION

The present invention relates generally to terahertz (THz) imaging systems, and more particularly to such imaging systems that can acquire images in real-time at video rates, e.g., by utilizing a coherent narrow-band THz illumination source.

The transparency of materials to radiation having frequencies in a range of about 0.1 to about 10 terahertz (THz) can be quite different than their transparency to radiation having frequencies in the visible range. For example, germanium, silicon, polytetrafluoroethylene plastic (Teflon), high and low-density polyethylene plastics (HDPE and LDPE), teeth, leaves, clothing and envelopes typically become more transparent at these terahertz frequencies. The increased transparency of many materials at terahertz frequencies has prompted the development of a variety of terahertz imaging systems. However, conventional imaging systems often obtain an image of an object by linearly scanning the object through a tightly focused THz beam—a practice that limits the image acquisition time to the mechanical scan rate of the system. With upper limits of hundreds of pixels per second for acquiring an image by mechanical scanning, in this approach, a complete image requires minutes to be acquired.

Alternatively, conventional terahertz imaging systems suitable for acquiring real-time images (e.g., 20 frames per second or more) typically employ an electro-optic crystal for frequency upconversion of THz pulses to optical pulses so that a CCD focal-plane camera can be employed for detecting the radiation and generating images. This arrangement, however, requires precise timing of optical and THz pulses, thus necessitating a scanning delay mechanism that adds to system complexity. Moreover, such systems are inherently broadband (typically short THz pulses (e.g., less than 1 ps) are utilized that result in a bandwidth larger that 1 THz), and hence not suitable for applications that require coherent narrow-band illuminating radiation for frequency-sensitive imaging.

Accordingly, there is a need for an enhanced terahertz imaging system that can provide real-time, high resolution images.

SUMMARY OF THE INVENTION

In one aspect, the present invention provides a terahertz (THz) imaging system that includes a source for generating radiation having one or more wavelengths in a range of about 0.1 THz to about 10 THz (e.g., in a range of about 1 to about 10 THz or in a range of about 2 to about 5 THz), and a bolometer detector for detecting radiation generated by the source. The imaging system can also include an optical system disposed between the source and the detector for directing radiation from the source onto the detector. In many embodiments, the bolometer detector can include a plurality of uncooled bolometer elements (e.g., arranged as a one or a two-dimensional array) for detecting radiation in a range of about 0.1 THz to about 10 THz.

In another aspect, the radiation source is capable of generating radiation having a power greater than about 1 milliwatt (mW), for example, a power in a range of about 1 mW to about 100 mW, or in a range of about 5 mW to about 100 mW (e.g., in a range of about 1 mW to about 10 mW or in a range of about 5 mW to about 10 mW). It has been unexpectedly discovered that terahertz radiation at the above-specified wavelength ranges and power levels can be used with conventional bolometer detectors to obtain direct transmission images (or reflectance images) at resolutions and acquisition rates sufficient for real-time monitoring and screening applications.

In a related aspect, the imaging system can include an imaging plane where an object to be imaged can be disposed. Further, the imaging system can acquire an image of the object in real-time at a rate of at least about 20 frames per second (e.g., 60 frames per second). The images can be used directly or accumulated to further improve image quality, e.g., by reducing noise.

In another aspect, the bolometer detector, which can include an array of bolometer detecting elements, can comprise a vanadium oxide film as its radiation sensing element. Alternatively, the radiation energy absorbing element can be formed of a semi-metal, e.g., bismuth. The bolometer can be further "tuned" to a desired frequency band (e.g., from about 0.1 THz to 10 THz, more preferably from about 2 THz to 5 THz) by employing a reflecting backplane placed about $\lambda/4$ away (where $\lambda$ is about 30-3000 microns) and chosen to correspond generally with the frequency of the THz illumination source.

A variety of terahertz radiation sources can be employed in the imaging system. In many embodiments, the imaging system can include quantum cascade lasers (QCL) for generating continuous wave (CW) radiation with frequency components in a range of about 1 to about 10 THz. Other terahertz radiation sources can also be employed. For example, in an exemplary embodiment described below, the radiation source includes a far-infrared laser that generates 2.52 THz radiation via a methanol vapor medium pumped by radiation from a $CO_2$ laser.

In another aspect, the optical system for directing radiation from the source to the bolometer can include optical elements (e.g., mirrors, lenses) for directing radiation from the source to an object to be imaged to cause its illumination (e.g., backlighting the object), and can further include other optical elements for directing at least a portion of the radiation transmitted through the object or reflected from the object onto the bolometer detector so as to generate an image of the object.

In another aspect, a terahertz imaging system is disclosed that includes a source of terahertz radiation (e.g., a QCL) generating radiation pulses having one or more frequency components in a range of about 0.1 THz to about 10 THz, and an optical system for directing the radiation pulses to an object to be imaged. The system further includes an array of radiation detecting elements for detecting the THz radiation transmitted through the object (or reflected by the object) to generate detection signals. The radiation detecting elements are further adapted to generate reference signals in response to detection of unwanted ambient infrared radiation in absence of the THz radiation. The term "in the absence of THz radiation" is intended to encompass the cases in which the THz radiation (and/or its effect on the detector) is not present, or the THz radiation (and/or its effect on the detection elements) is substantially attenuated (e.g., less than about 10 percent, and preferably less than about 5 percent of the value in presence of the THz pulses). The imaging system further includes a processor that is in communication with the detection array to generate a THz image of the object based on a difference between said detection and reference signals. For example, the processor can subtract a reference signal generated by each detection element from a detection signal generated by that element to form the THz image, thus greatly reducing the effect of the ambient infrared radiation.

In a related aspect, in the above THz imaging system, the array of detecting elements can generate the detection and reference signals during at least two different temporal periods, e.g., during two consecutive temporal periods. By way of example, the duty cycle of the pulses can be configured such that during at least a portion of one period, the pulses are applied to the object and during the other period, they are not.

In further aspects, the detecting elements can be bolometer detecting elements (e.g., uncooled), and the imaging system can be capable of generating images in a range of about 20 to about 60 images per second.

In another aspect, a terahertz imaging system is disclosed that includes a plurality of terahertz radiation sources that are capable of generating radiation at different frequencies in a range of about 0.1 THz to about 10 THz, and an optical system for directing the radiation from those sources to an object to be imaged. The imaging system further includes a controller, which is in communication with the sources, for selectively activating them to illuminate the object at different frequencies. An array of radiation detecting elements are disposed to detect at least a portion of the radiation that is transmitted through the object (or reflected by the object) so as to generate at least two images of that object corresponding to two of those frequencies. The different frequencies generated by the sources can correspond to two discrete frequencies, or two frequency bands (either disjoint or partially overlapping) centered about two discrete frequencies.

In other aspects, in above multi-frequency THz imaging system, the radiation sources can comprise quantum cascade lasers, and the radiation detecting elements can comprise bolometer detection elements.

Further understanding of the invention can be obtained by reference to the following detailed description in conjunction with the associated drawings discussed briefly below.

DETAILED DESCRIPTION

Figure 1A:
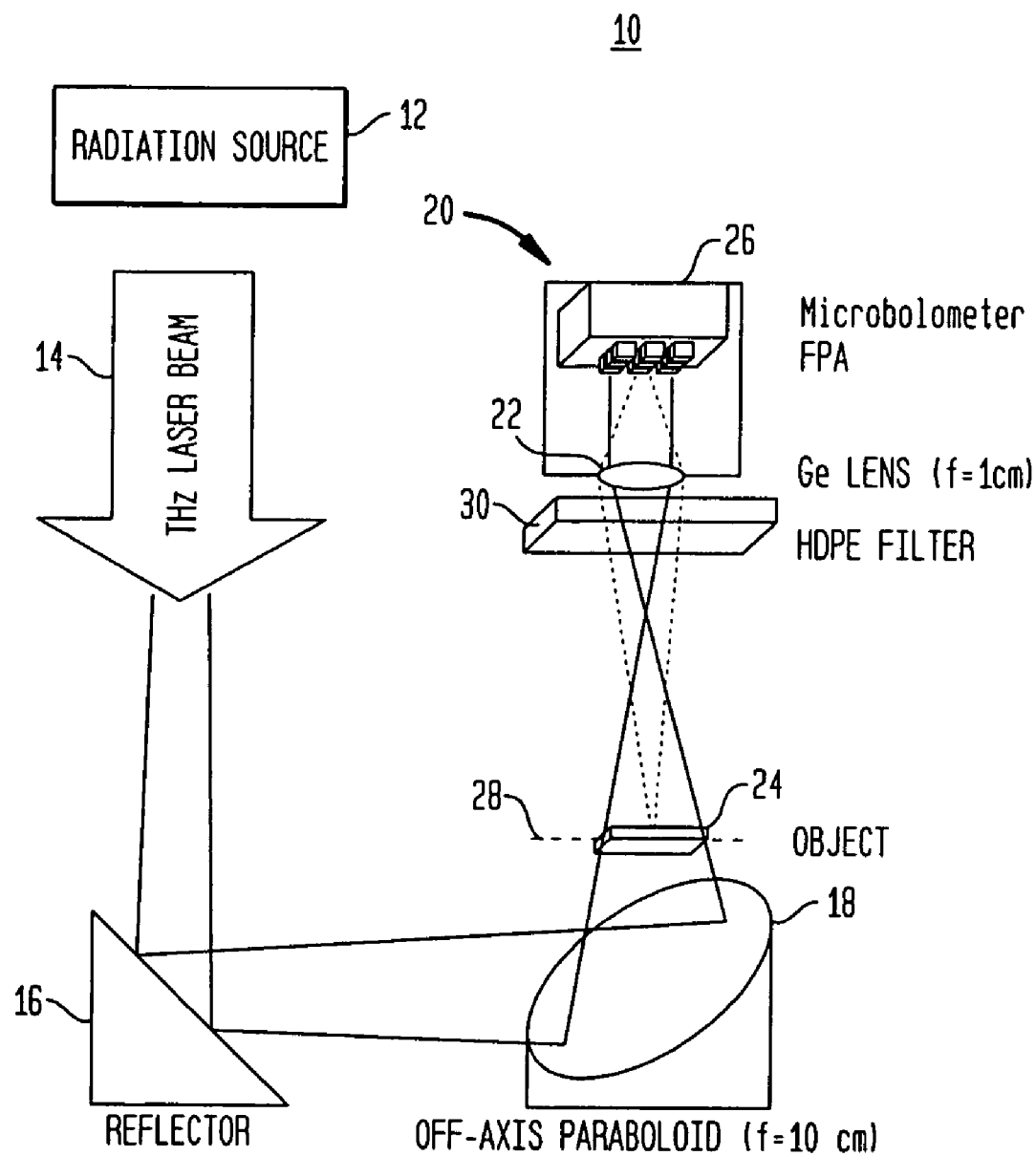
FIG. 1A schematically illustrates an exemplary terahertz imaging system in accordance with one embodiment of the present invention, FIG. 1B schematically depicts an element of a microbolometer array.

FIG. 1A schematically illustrates a terahertz imaging system 10 according to an exemplary embodiment of the invention that includes a source 12 for generating radiation having one or more frequency components in a range of about 0.1 terahertz (THz) to about 10 THz (corresponding to a wavelength range of about 30 to about 3000 microns). In many embodiments, quantum cascade lasers (QCLs) are employed for generating the terahertz radiation (e.g., continuous-wave (CW) or pulsed radiation). Some examples of quantum cascade lasers suitable for use in the practice of the present invention as terahertz radiation sources are described in copending applications of the assignee of the present application entitled "Terahertz Lasers and Amplifiers Based on Resonant Optical Phonon Scattering to Achieve Population Inversion" (filed on Sep. 12, 2003 and having an application Ser. No. 10/661,831) and "Metal Waveguides for Mode Confinement in Terahertz Lasers and Amplifiers" (filed on Sep. 12, 2003 and having an application Ser. No. 10/661,832), both of which are herein incorporated by reference in their entirety. At frequencies below about 1 THz, Gunn oscillator pumped frequency multipliers can be used, for example, as a coherent radiation source in the practice of the invention.

In one exemplary embodiment, however, a far-infrared gas laser manufactured by Laser Photonics of Lake Mary, Fla. under trade designation S122, which operates at room temperature, is utilized as the radiation source 12. This far-infrared laser generates continuous wave (CW) 2.52 THz (118.8 micron) radiation via a $CH_3OH$ (methanol) vapor pumped by a $CO_2$ laser, producing approximately 10 mW of output power. It should be understood that the invention can be practiced with any suitable radiation source that can provide radiation with frequency components in a range of about 0.1 THz to about 10 THz and at a sufficient power level for a desired application.

In this exemplary embodiment, a terahertz laser beam 14 generated by the laser 12 is allowed to expand over a path length of about 1.5 m at a divergence angle of 1.4° associated with the laser, resulting in a beam diameter of about 4.5 cm. A reflector 16 disposed at a selected position along the expansion path of the laser beam reflects the radiation beam toward an off-axis paraboloid mirror 18, which receives the 4.5 cm diameter beam. In this embodiment, the paraboloid mirror 18 has a focal length of about 10 cm (f=10 cm). The exemplary imaging system 10 further includes an uncooled bolometer imaging device 20 that includes a germanium camera lens 22 for collimating the radiation beam (after passage through an object 24 to be imaged as discussed below) onto a detector 26 comprising a two-dimensional array of microbolometer elements, as discussed in more detail below. The term "bolometer detector" is known to those having ordinary skill in the art. To the extent that any further explanation may be needed, a "bolometer detector" refers to a radiation detection device that can include a sensitive element capable of exhibiting a change in some measurable property (e.g., electrical resistance) in a response to a change in its temperature. Although in many embodiments of the invention (including this exemplary embodiment), an uncooled bolometer detector (i.e., a bolometer detector capable of operating at room temperature (about 25° C.)) is employed, in other embodiments, cooled bolometer detectors, e.g., detectors cooled to cryogenic temperatures, can be utilized. It should also be understood that bolometer detectors suitable for use in the practice of the invention are not limited to those that exhibit a change in their electrical resistivity in response to a temperature change, but can also include other types of bolometer detectors, e.g., pyroelectric or thermoelectric detectors.

In this embodiment, the lens 22 has a focal length of about 1 cm (f=1 cm) and an anti-reflection (AR) coating for minimizing reflections of radiation at its surfaces. Although in this illustrative embodiment the AR coating is suitable for minimizing lens surface reflections at about 10 microns, more preferably, the AR coating is selected to be maximally effective at the wavelength of the radiation generated by the source.

With continued reference to FIG. 1, the object 24 to be imaged can be disposed at an image plane 28 of the lens, which in this embodiment is located 10 cm in front of the lens. The beam reflected by the paraboloid mirror 18 can back-illuminate a sample area of the object 24 (e.g., an area of roughly 4×4 $cm^2$), which can encompass a portion or the entire cross-section of the object. The terahertz radiation transmitted through the object is then collimated by the fast F/1 camera lens 22 to impinge on the micro-bolometer array 26. In this embodiment, the lens 22 is positioned about 1 cm behind the focal point of the off-axis paraboloid mirror. This results in under-filling of the 1-cm diameter lens and in illuminating only about 40% of the detector elements. Such concentration of the signal over a fraction of the detector area can improve the signal-to-noise ratio (SNR). For example, in exemplary terahertz images describe below, which were obtained by employing this exemplary system, at the brightest illumination point (typically the center of the image) the SNR was estimated to be about 13 dB, decreasing towards the edges where the signal diminishes.

In this exemplary embodiment, a filter 30 in the form of a sheet of high density polyethylene having a thickness of about 6.5 mm (2.4 dB insertion loss) is placed directly in front of the bolometer camera to provide a uniform background. As discussed below, the microbolometer array detector utilized in this exemplary embodiment has a high sensitivity at wavelengths of about 10 microns (NETD of about 40 mK). Accordingly, in the absence of the filter, the uneven ambient blackbody radiation (at a temperature of about 300 K) can degrade the SNR of the images obtained by the bolometer detector. Those having ordinary skill in the art will appreciate that the filter 30 may not be needed in embodiments in which the detector exhibits a peak sensitivity at wavelengths far removed from the peak of the ambient black body spectrum.

In this embodiment, the detector camera 20 is an uncooled, microbolometer focal-plane array camera manufactured by BAE Systems of Lexington, Mass. under trade designation SCC500L. The camera employs a 160×120 element array of microbolometers, spaced at a pitch of 46.25 microns. Each microbolometer includes a thin film of vanadium oxide (VOx) on a silicon nitride airbridge, with a reflecting back plane placed at about λ/4 away. The microbolometers are designed for operation in the 7.5-14 micron 'night vision' band with a thermal fluctuation noise-equivalent power (NEP) rated at $9 \times 10^{-13}$ W/$\sqrt{Hz}$, resulting in a noise-equivalent temperature difference (NETD) (including F/1 optics) of about 40 mK in this band.

It was discovered unexpectedly that despite its design for operation in the 7.5-14 micron band, an uncooled microbolometer camera can be employed to obtain terahertz images at a much longer wavelength of about 118.8 microns (a frequency of about 2.5 THz), albeit at a lower sensitivity. Accordingly, in the exemplary imaging system 10, this camera is utilized as a staring focal-plane array for recording images of the object 24.

Figure 1B:
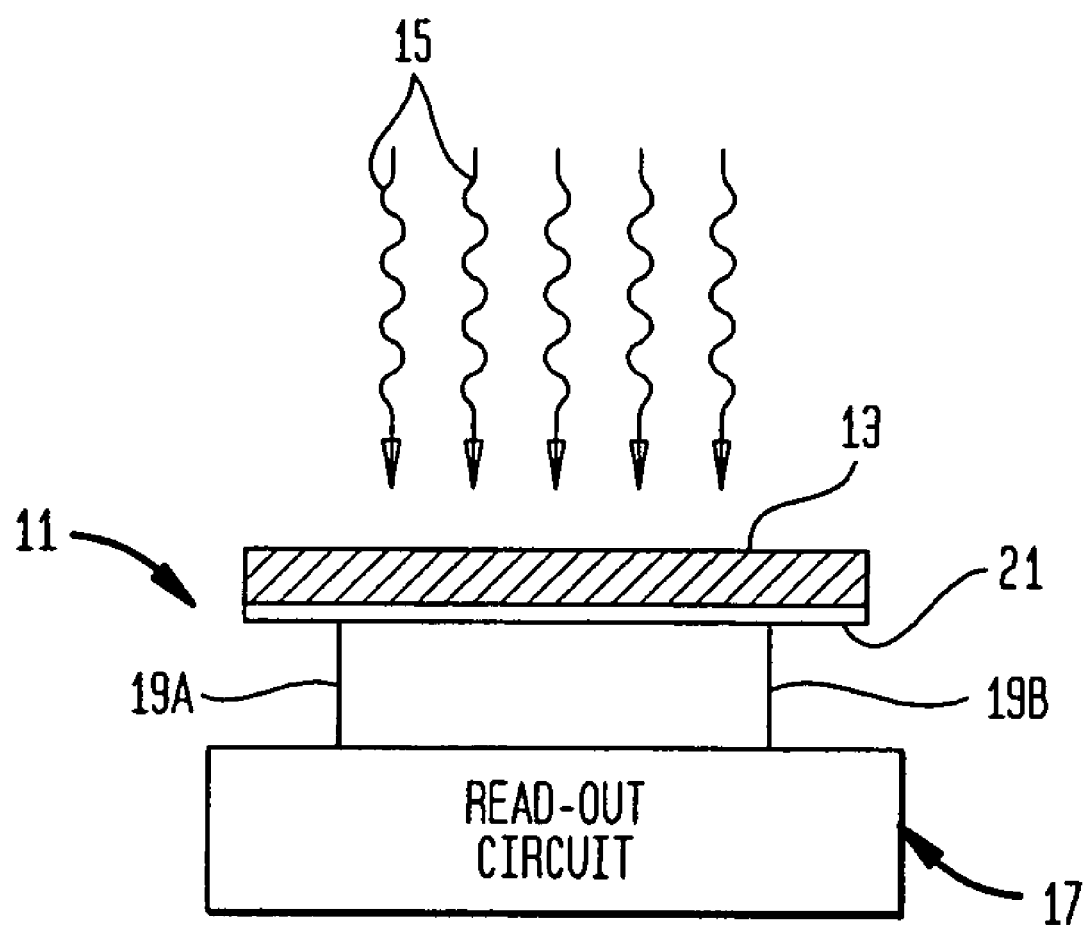

As shown schematically in FIG. 1B, a detection element (pixel) 11 of a microbolometer array can include a sensing element 13 that can be heated by incoming radiation 15, and a readout element 17 (e.g., incorporated in a semiconductor substrate) that is electrically coupled to the sensing element via electrodes 19a, 19b to detect a change (e.g., resistivity, pyroelectric effect, etc) in the sensing element in response to its temperature change. A reflecting backplate 21 can also be provided to enhance the detection efficiency.

In some embodiments, the images captured by the terahertz imaging system 10 can be transferred to a computer (not shown) for storage and/or image analysis.

Figure 2A:
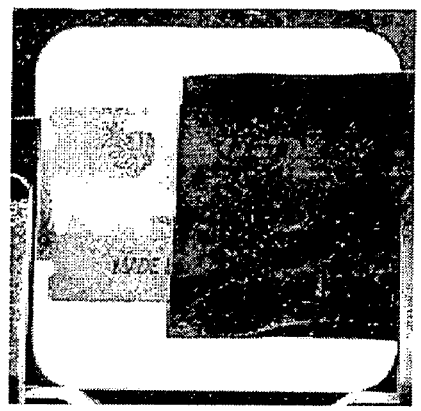
FIG. 2A shows an image of a partially covered razor blade obtained by employing visible radiation.
Figure 2B:
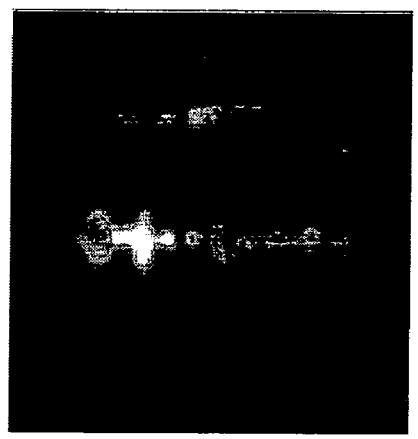
FIG. 2B shows a single frame of a real-time THz video image of the scene shown in FIG. 2A obtained by employing an exemplary terahertz imaging system according to one embodiment of the invention.
Figure 2C:
FIG. 2C shows a terahertz image of the razor blade of FIG. 2B obtained by averaging 30 frames, FIG. 3 schematically illustrates a THz imaging system according to another embodiment of the invention in which a QCL is employed as the radiation source, FIG. 4 schematically depicts the response of a bolometer to a pulse of THz radiation over three image frames acquired by the camera utilized in the imaging system of FIG. 3.

As an illustration of the efficacy of the above system 10 for obtaining terahertz images and their comparison with visible images, FIGS. 2A-2C show visible and terahertz images of a double edged razor blade, which is partially covered by a visibly opaque sheet of black low density polyethylene (LDPE, 50 micron thickness, 1.1 dB insertion loss). More specifically, FIG. 2A shows a visible image of the covered razor blade in a metal frame and FIG. 2B shows a single frame of a real-time video of the same scene obtained by employing the above imaging system 10 with the THz radiation source backlighting the razor blade. The acquisition time for obtaining this image was about 16 milliseconds (ms) (due to the use of an analog video signal, the image exhibits noticeable interlacing (horizontal lines)). FIG. 2C shows a terahertz image of the razor blade obtained by averaging 30 frames of the same scene, thus reducing the interlacing noise and improving slightly the signal-to-noise ratio. Even with this level of signal averaging and a reduced number of illuminated pixels, the exemplary imaging system exhibits an equivalent linear scan rate of about $1.4 \times 10^4$ pixels/second, which is more than about two orders of magnitude faster than a mechanically scanned system.

In FIGS. 2B and 2C, the detailed interior features and edges of the razor can be seen, as well as the contours of the black LDPE sheet. A contrast difference can also be seen between the uncovered and covered portions of the interior of the razor, due to the insertion loss of the black LDPE. The resolution of this exemplary terahertz imaging system can be compared to the Rayleigh criterion, which states that the minimum resolvable angle is: $\theta \approx 1.22\ \lambda/d$, where $\lambda$ is the wavelength, and d is the 1-cm diameter of the germanium camera lens. At the image plane, which in this embodiment is about 10 cm in front of the lens, the Rayleigh criterion limits the resolution to about 1.5 mm. In the terahertz images, 2-mm features of the razor (marked with arrows in FIG. 2A) are resolvable, indicating the imaging system is capable of generating near diffraction-limited images. It should be understood that since human eyes are more sensitive to moving objects, the real-time images of a moving target displayed on a monitor can be more impressive than the still images of FIGS. 2B and 2C might suggest.

It should be understood that the above images are provided only for illustrative purposes and are not intended to necessarily indicate optimal capabilities of a terahertz imaging system formed in accordance with the teachings of the invention. For example, in other embodiments, significant improvements in SNR and spatial resolution can be obtained by utilizing focal-plane microbolometer cameras optimized for detecting radiation in a range of about 0.1 to about 10 THz. For example, such bolometer cameras can include radiation-absorbing sensing materials that are more suitable for converting energy of radiation in a range of about 0.1 to about 10 THz into heat. By way of example, such energy absorbing materials can be formed of semi-metals, such as bismuth, e.g., in the form of a sheet whose resistance is close to about 200 ohms ($\Omega$), which is well-matched to the free-space impedance of about 377 ohms for efficient energy absorption.

In addition, placing a reflecting backplane at a distance of $\lambda/4$, where $\lambda$ corresponds to the wavelength of radiation (e.g., wavelengths in a range of about 30 to about 3000 microns corresponding to frequencies in a range of about 0.1 to about 10 THz) can improve the signal-to-noise ratio. In addition, utilizing an anti-reflection coating designed for the wavelengths of interest and utilizing larger bolometer elements can also enhance the performance of terahertz imaging systems according to other embodiments of the invention relative to the exemplary embodiment described above.

In some embodiments, the THz radiation reflected from an object can be used to generate an image of the object. For example, a lens can be positioned between an the object and a bolometer array to collect at least a portion of the THz radiation reflected from an illuminated surface of the object and to focus the collected radiation onto the bolometer array for generating a reflectance image of the object. Such an embodiment can be utilized, e.g., to determine frequency dependent reflection properties of an object.

In many embodiments, the radiation source can be a solid state quantum cascade laser (QCL) that can be tightly packaged with the other components to provide a compact terahertz imaging system. In particular, dimensionally compact quantum cascade lasers (e.g., having dimensions of about $10 \times 40 \times 1350$ micron$^3$) can be fabricated by utilizing the teachings of the above-referenced patent applications. Such quantum cascade lasers require only a bias voltage to generate single frequency terahertz radiation. Further, such quantum cascade lasers can generate continuous wave (CW) radiation at operating temperatures (e.g., 40K or 120K) that can be maintained by utilizing, e.g., closed-cycle, pulse tube cryorefrigerator. In some embodiments, the compact imaging system can provide frequency agility by incorporating several quantum cascade lasers, each generating radiation at a different frequency.

Figure 3:
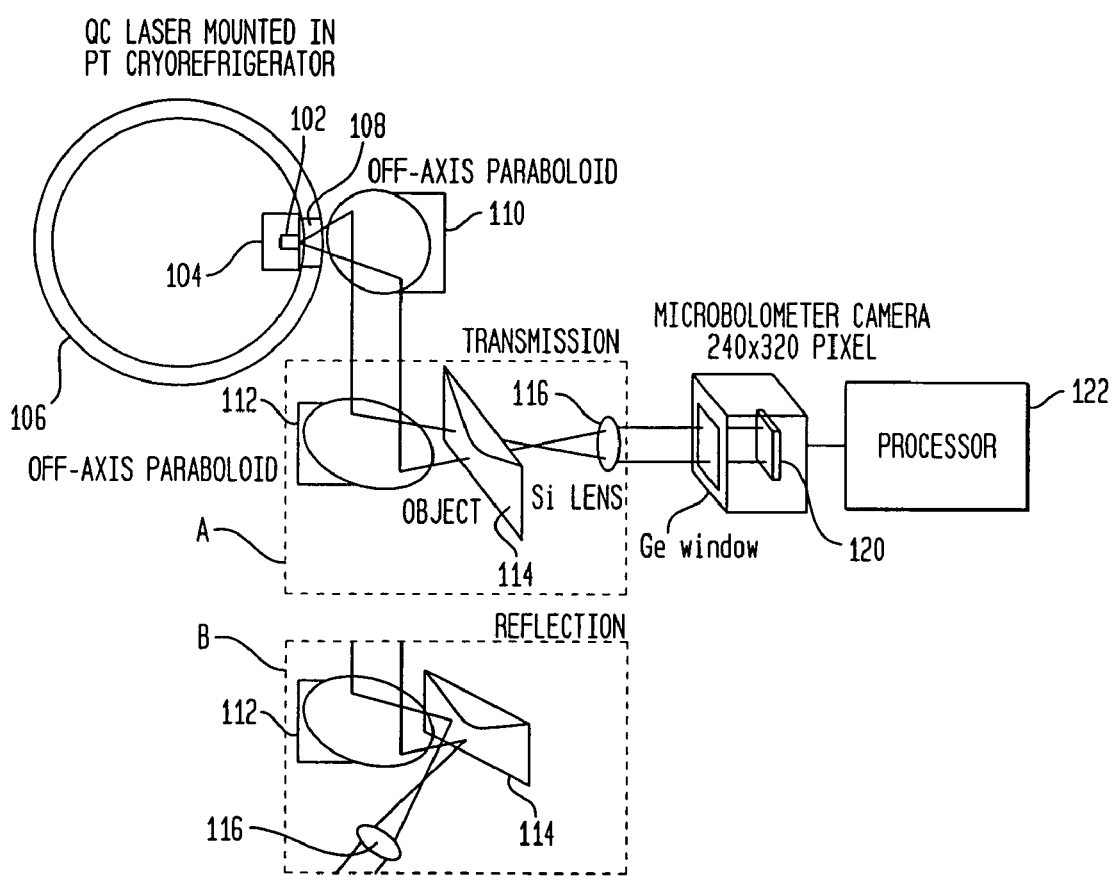

For example, FIG. 3 schematically depicts another embodiment of a terahertz imaging system 100 according to the teachings of the invention that employs a QCL 102 as the radiation source. The QCL can be employed in a continuous-wave (CW) mode or a pulse mode. For example, as discussed in more detail below, the QCL can be utilized in a pulse mode in conjunction with a differencing scheme to attenuate, and preferably remove, the effect of the infrared background radiation on the detector's signal. In this embodiment, the QCL 102 can produce radiation at a frequency of 4.3 THz with a maximum CW power of 125 mW at an operating temperature of about 10 K. When operated in a pulse mode at a temperature of about 33 K at a duty cycle of about 25%, the peak power can be about 50 mW. The QCL can be fabricated, e.g., by utilizing molecular beam epitaxy to grow precise thicknesses of semiconductors layers based on resonant-phonon depopulation scheme as disclosed in the above-referenced patent applications, which are herein incorporated by reference. In this embodiment, the QCL was fabricated as a 98 micron by 2.15 mm semi-insulating surface-plasmon ridge waveguide with its rear facet coated with a high-reflectivity coating.

With continued reference to FIG. 3, in this embodiment, the QCL 102 is mounted, e.g., via indium soldering, to a copper carrier 104, which is, in turn, mounted in a cryorefrigerator 106 having a radiation transmissive window 108 (e.g., a polypropylene window). Due to high angular divergence of the emitted laser beam, the laser is preferably disposed as close as possible to the window. An f/1, 50-mm off-axis parabolic (OAP) mirror 110 collimates the emerging laser beam, and a second OAP (f/2) 112 (shown in insert A) focuses the collimated beam so as to back-illuminate an object 114 (e.g., an envelope in this embodiment). In many embodiments, the angle subtended by the OAP 110 determines the fraction of light emerging from the window 108 that reaches the object (e.g., 85% the light can reach the object). In this embodiment, the illuminated area of the object 114 can be about 3×3 cm$^2$, although other illumination areas can also be utilized (e.g., by selecting an appropriate diameter of the OAPs 110 and 112). At least a portion of the light is transmitted through the object. A focusing lens 116 (e.g., an f/1, 25-mm diameter Si meniscus lens) focuses the transmitted light, through a Ge vacuum window, onto a microbolometer focal-plane array camera 120. By way of example, in some embodiments, a commercial 320×240 pixel, uncooled, vanadium oxide (VOx) microbolometer focal-plane array camera marketed by BAE systems of Lexington, Mass. under trade designation SCC500 can be employed. In some embodiments, the surfaces of the lens 116 and the Ge vacuum window are coated with a thin layer of an anti-reflection coating material (e.g., a thin sheet of polyethylene) to improve transmission of the radiation through these elements (e.g., an improvement in a range of about 20 to 40% can be obtained).

Alternatively, as shown schematically in the insert B of FIG. 1, the apparatus can be configured to operate in a reflection, rather than a transmission, mode. More specifically, the focusing element 116 and the camera 120 can be disposed so as to detect at least a portion of the incident radiation that is reflected by the object 114. The imaging system can further include a processor 122 in communication with the camera to receive signals from the camera and process those signals for obtaining THz images, e.g., process the signals according the differencing scheme discussed below. Although in this embodiment the processor is depicted separate from the camera, in other embodiments it can be integrated with the camera.

Figure 4:
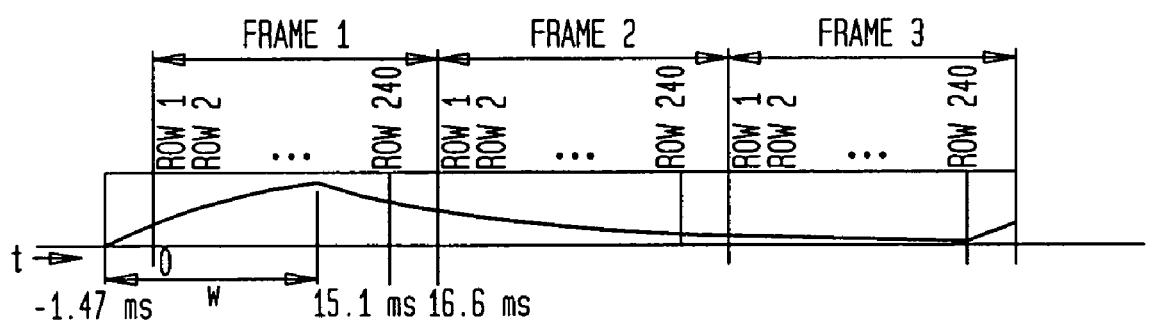

An exemplary sampling sequence utilized in the focal-plane array of the camera 120 is schematically depicted in FIG. 4. Pixels in a row are sampled simultaneously while pixel signals in different rows are acquired sequentially, with a 64 microsecond time interval for sampling of each row. An inactive time period of 1.47 ms follows the sampling of the last row (#240 in this case). In this exemplary embodiment, the focal plane is sampled at a 60-Hz frame rate (16.6 ms per frame). It should be understood that in other embodiments, other sampling sequences and sampling rates can be employed.

Because microbolometers are generally sensitive to both terahertz as well as infrared radiation, in some embodiments (e.g., those in which the QCL operates in a CW mode), the infrared background is suppressed by utilizing a long-wavelength-pass filter (e.g., by disposing such a filter in front of the camera). Alternatively, in some other embodiments, a differencing scheme is utilized in which a reference frame obtained in presence of infrared background radiation but in absence of the terahertz radiation (or with only attenuated levels of terahertz radiation present) is subtracted from a frame in which the terahertz radiation is detected. For example, the QCL can be operated in a pulse mode and the camera signal in an image frame in absence of the THz radiation (or at significantly attenuated levels of the THz radiation) can be subtracted from a signal frame in which at least a portion of the laser pulse is transmitted (or reflected) by an object to be incident on the camera, so as to attenuate (and preferably remove) the common-mode infrared background signal. For example, such a differencing scheme can be understood by reference to FIG. 4. In this example, the detector signal (modeled as a solid trace) results from a THz laser pulse of width w, which causes a temperature increase in the microbolometers of the camera. The laser pulse is applied at t=−1.47 ms to cause a signal rise with about 13 ms thermal time constant until the end of the pulse, where the signal decays with the same time constant. In frame 1, both THz and infrared background signals are present, whereas in frame 3 the THz signal has significantly decayed. Thus, subtracting frame 3 from frame 1 results in cancellation of the common-mode infrared signal from the combined THz/infrared signal present in frame 1. In this embodiment, the delay between the signal frame and the reference frame is limited to one frame (i.e., frame 2) so as to minimize, and preferably avoid, introduction of additional 1/f and/or motion noise. In many embodiments, sufficiently high frame rates (e.g., 20 Hz) together with the aforementioned differencing scheme can be utilized to perform real-time imaging, e.g., at a frame rate in a range of about 20 Hz to about 60 Hz, or 30 Hz to 60 Hz.

Figure 5A:
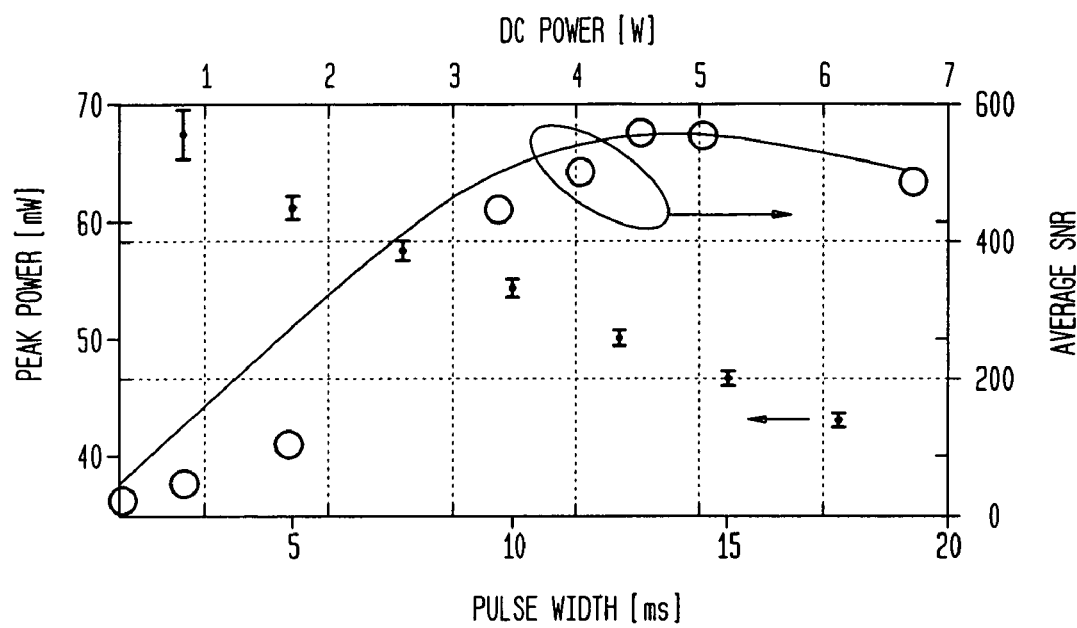
FIG. 5A depicts a graph illustrating peak power of a QCL operating in a pulse mode, utilized in one embodiment of the invention (e.g., the embodiment of FIG. 3), as a function of pulse width.
Figure 5B:
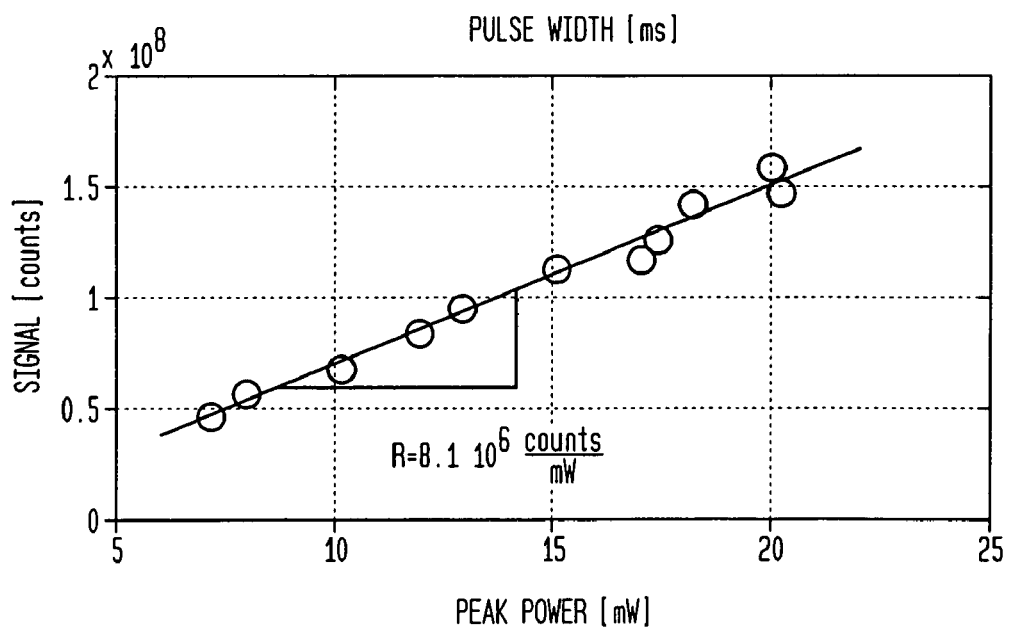
FIG. 5B depicts a graph illustrating signal intensity of a detector array as a function of peak pulse power in an embodiment utilizing a QCL having the peak power v. pulse width characteristic shown in FIG. 5A, FIG. 6 schematically illustrates an experimental set-up suitable for measuring the graph of FIG. 5B.

As noted above, in many embodiments in which the above differencing scheme is utilized, the QCL is operated in a pulse mode. By way of example, FIG. 5A shows a graph depicting the peak power, P, emitted by an embodiment of the QCL 102 as measured at the cryorefrigerator window 108 as a function of pulse width. The graph shows the peak power decreases with pulse width due to heating of the QCL's active region. When utilizing the above differencing scheme, the pulse width of the QCL can be optimized so as to maximize the differential signal-to-noise ratio (SNR) by considering the time constant of the detector's response in relation to the frame rate, as shown in FIG. 5A. FIG. 5B presents a graph depicting camera's signal intensity (in terms of counts) as a function of the peak power of pulses.

Figure 6:
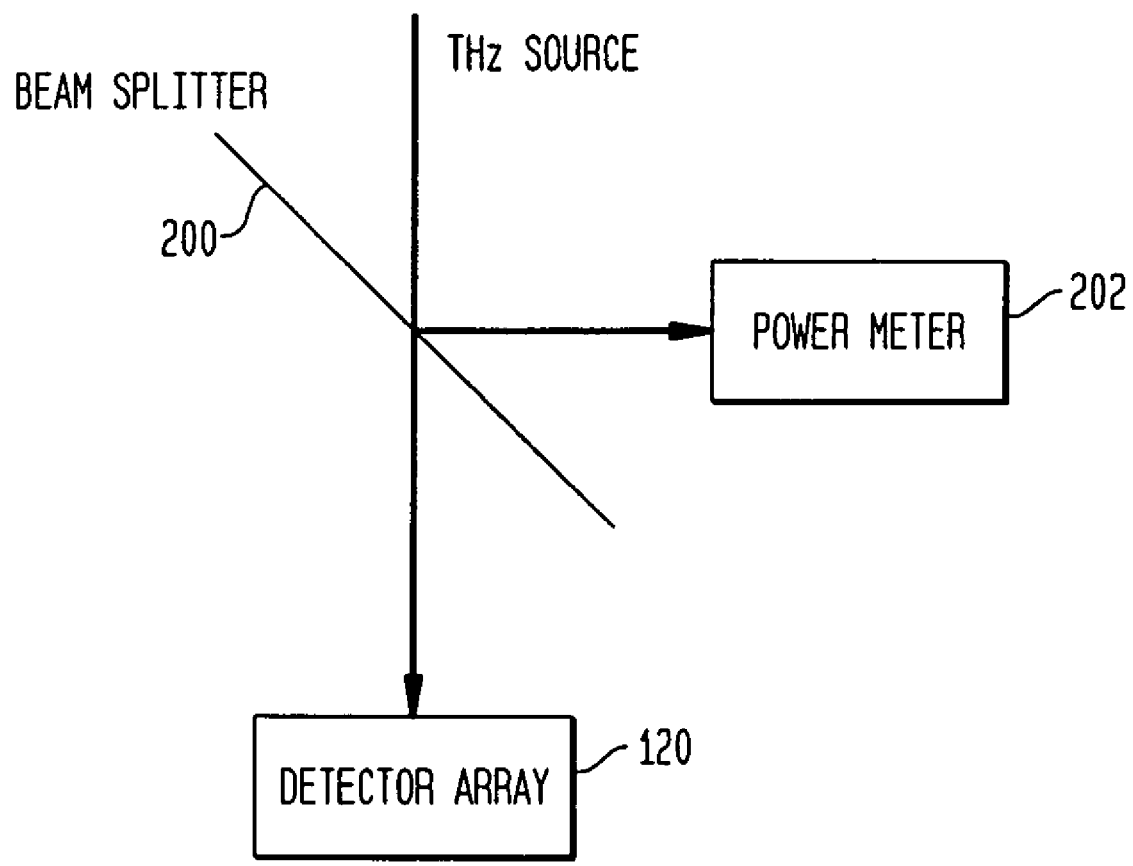

By way of example, in one embodiment in which the aforementioned QCL operating at a frequency of 4.3 THz was utilized in a pulse mode, together with a bolometer detector exhibiting the signal v. time response depicted in the above FIG. 4, the highest signal-to-noise ratio (about 340 and 550 with and without the Si lens 116, respectively) was obtained at a pulse width of about 13.5 ms. The SNR was defined as the spatially and temporally averaged signal, <x>, divided by the root-mean-square (RMS) noise (σ). The rms noise can be determined, e.g., in a single frame (e.g., 20 Hz bandwidth in this example) in the absence of the THz radiation. In this example, an optical noise equivalent (NEP$_0$) of about 320 pW/$\sqrt{Hz}$ was measured. The NEP$_0$ can be defined in accordance with the following relation:

$$NEP_0 = \frac{\sigma_{1Hz}}{R},$$

where $\sigma_{1Hz}$ is the rms noise normalized to a 1 Hz bandwidth, and R denotes a differential responsivity, which can be obtained experimentally by utilizing, e.g., a measurement set-up shown schematically in FIG. 6. More specifically, this set-up can be employed to measure the change of detector signals with respect to incident power. The incident power is measured by employing a beam-splitter 200 to divert a portion of the laser beam to a power meter 202.

Figure 7A:
FIG. 7A shows a visible image of the letters "MIT" written in pencil on inner surface of a paper security envelope.
Figure 7B:
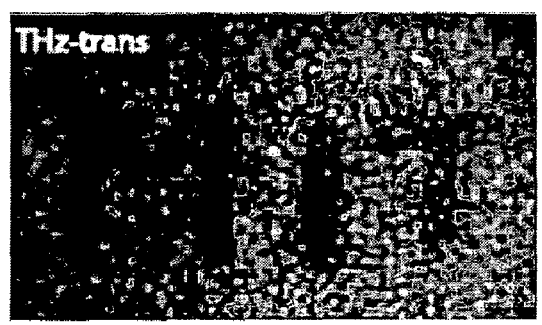
FIG. 7B shows a single THz differential image frame of the envelope shown in FIG. 7A obtained in transmission mode by employing an embodiment of an imaging system of the invention operating at 4.3 THz.
Figure 7C:
FIG. 7C shows a THz differential image of the envelope shown in FIG. 7A obtained in reflection mode by averaging 20 image frames of the envelope acquired by an embodiment of an imaging system of the invention operating at 4.3 THz.
Figure 7D:
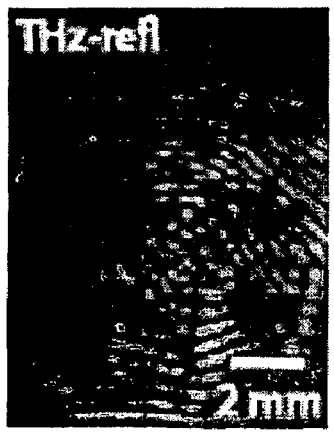
FIG. 7D shows a 20-frame average THz image of a thumb print acquired by employing an imaging system according to one embodiment of the invention, and FIG. 8 schematically shows a multi-frequency THz imaging system in accordance with one embodiment of the invention having a band of quantum cascade lasers suitable for use in some embodiments of the invention in which the QCL elements provide radiation at different frequencies.

By way of example and only for illustration purposes, the above imaging system 100 was utilized to demonstrate the feasibility of the use of imaging systems of the invention for screening mail. The letters "MIT" were written in pencil on the inside of a paper security envelope (which exhibits about 14 db loss at 4.3 THz), as shown at visible frequencies in FIG. 7A. FIG. 7B shows a single THz differential frame of the envelope, obtained in transmission mode by employing an imaging system of the invention. FIG. 7C shows a THz differential image of the envelope obtained in reflection mode by averaging 20 frames. To obtain the reflected image, half of the envelope covering the letters was wedged slightly to prevent a strong specular reflection from the first surface. Further, to show high resolutions attainable in THz images obtained by the systems of the invention, FIG. 7D shows a reflected THz, 20-frame average image of an ink thumb print of one of the inventors on a polyethylene wedge. The distance between the grooves of the thumb print is about 500 microns, thus illustrating the high resolution of the image. The above images can be viewed in real-time at video rates, where the integration of the eye and pattern recognition of the brain further enhance their perceived quality.

It should be understood that the above images are presented only for illustration purposes, and are not necessarily intended to indicate the optimal results that can be obtained by employing a THz imaging system of the invention to acquire THz images of an object.

Hence, in many embodiments, the terahertz imaging systems of the invention are capable of performing real-time video imaging at a specific THz frequency—a capability not generally exhibited by currently available THz imaging systems. For example, the image acquisition speed of a terahertz imaging system of the invention can be more than about two orders of magnitude faster than that of a conventional mechanically scanned system. These imaging systems provide other advantages, as well. For example, they generally do not include any moving parts and can incorporate quantum cascade lasers that are compact and operable at a plurality of frequencies.

Figure 8:
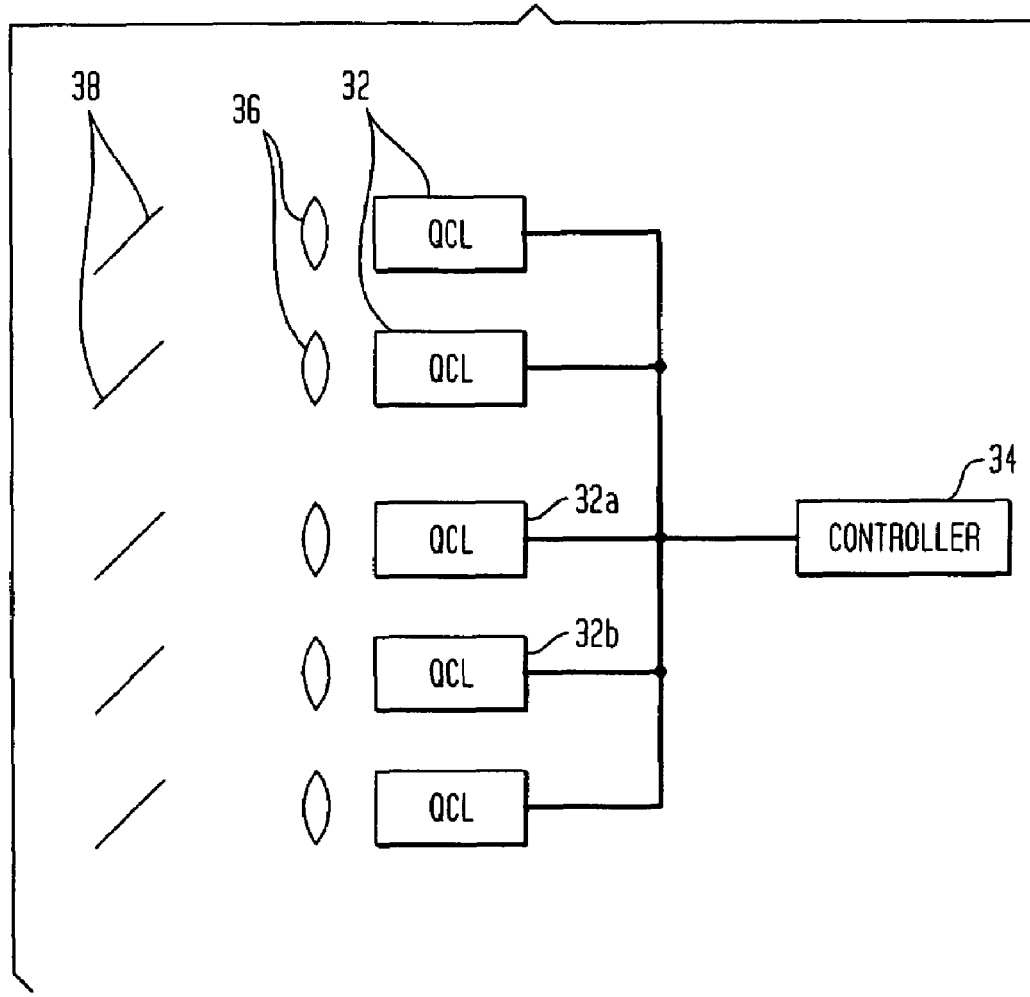

In some embodiments, a terahertz imaging system of the invention can include a multi-frequency terahertz radiation source that facilitates frequency-sensitive THz imaging in real-time. For example, as shown schematically in FIG. 8, such a radiation source can include a bank of quantum cascade laser (QCL) elements 32 (e.g., in the form of a one-dimensional or a two-dimensional array) operating at different frequencies. For example, one of the QCL elements (e.g., element 32a) can operate at a discrete frequency in a range of about 1 to about 10 THz while another QCL element (e.g., element 32b) can operate at a different frequency in this range. The choice of frequencies generally depends on the requirements of a specific application for which the terahertz imaging system is employed. In this embodiment, a controller 34 can selectively activate one or more of the quantum cascade lasers. Further, each of a plurality of lenses 36 can direct the radiation from a respective QCL to one of a plurality of reflective elements 38, which in turn directs the radiation to an object (not shown) to be imaged. At least a portion of the radiation transmitted through the object (or reflected by the object) is detected by an array of radiation detection elements (not shown) to generate images of the object corresponding to at least two of those frequencies.

Typically, the radiation frequencies correspond to spectral fingerprints of an object to be imaged. By way of example, by imaging the object at each frequency and comparing these images, the content of the image can be classified by shape and absorption frequency.

A terahertz imaging system according to the teachings of the invention can find a variety of applications. For example, such a system can be employed for inspection of structural plastics. Plastics such as Teflon and polyethylene, while typically opaque at very short wavelengths such as infrared and visible, are transparent in the terahertz frequency range. Hence, a terahertz imaging system of the invention can be utilized for real-time scanning of such plastics to identify defects, such as voids and cracks. Although such materials can be transparent at microwave frequencies (wavelength>3 mm), their terahertz images can provide a far greater resolution with a resolution of the order of one wavelength (e.g., about 100 microns). The inspection of a spray-on insulating foam utilized in NASA's space shuttle program on the shuttle's external tank is one example of such an application. The terahertz imaging of the foam can allow detecting voids in the foam as small as about 6 mm in diameter.

In another application, a terahertz imaging system of the invention can be employed for detection of contraband or toxic substances in envelopes. Some illicit drugs, such as methylenedioxymethamphetamine and methamphetamine, exhibit frequency-dependent absorption at terahertz frequencies, and are known to be distributed by mail in some cases. Hence, a terahertz imaging device of the invention can be utilized to screen mail for such illicit drugs or biological or chemical poisons. More specifically, envelopes, which are typically partially transparent to radiation at terahertz frequencies, can be imaged at different frequencies corresponding to the absorption spectra of the target substance. If significant absorption of the radiation were observed at these frequencies, a more definitive inspection of the envelope could be undertaken. Another application for which a terahertz imaging device of the invention can be employed includes detection of concealed weapons by utilizing transparency of clothing and reflectivity of metals to terahertz radiation. By utilizing their spectral fingerprints, plastic explosives can be detected at THz frequencies even though they cannot be detected by employing conventional x-ray imaging systems.

Those having ordinary skill in the art will appreciate that various changes can be made to the above embodiments without departing from the scope of the invention.

What is claimed is:

1. A terahertz imaging system, comprising
   a source for generating radiation having one or more frequencies in a range of about 1 THz to about 10 THz,
   a two-dimensional array of bolometer detector elements suitable for detecting radiation generated by said source, wherein a number of said detector elements in at least one of said dimensions is greater than about 120, and
   an optical system disposed between said source and said detector array for directing the radiation generated by said source onto said detector array,
   wherein each of said bolometer detector elements comprises a temperature sensitive element adapted to absorb at least a portion of said radiation generated by the source and convert said absorbed radiation into heat,
   wherein no antenna is utilized in said bolometer detector elements.

2. The imaging system of claim 1, wherein said bolometer detector comprises an array of uncooled bolometer detecting elements.

3. The imaging system of claim 1, wherein said radiation source generates radiation having a power in a range of about 1 mW to about 100 mW.

4. The imaging system of claim 1, wherein said radiation source generates radiation having a power in a range of about 5 mW to about 100 mW.

5. The imaging system of claim 1, wherein said imaging system comprises an image plane at which an object to be imaged can be disposed.

6. The imaging system of claim 5, wherein said optical system comprises one or more elements for directing the source radiation onto said object for illumination thereof and one or more elements for directing at least a portion of radiation transmitted through or reflected from said object onto said bolometer array elements so as to generate an image of said object.

7. The imaging system of claim 6, wherein said system is capable of acquiring images of said object at a rate of at least about 20 frames per second.

8. The imaging system of claim 7, wherein said system is capable of acquiring images of said object at a rate of about 60 frames per second.

9. The imaging system of claim 1, wherein said bolometer detector comprises a vanadium oxide film as a radiation sensing element.

10. The imaging system of claim 1, wherein said bolometer detector comprises a film of a semi-metal as a radiation sensing element.

11. The imaging system of claim 10, wherein said semi-metal comprises bismuth.

12. The imaging system of claim 1, wherein said source comprises a quantum cascade laser (QCL).

13. The imaging system of claim 12, wherein said quantum cascade laser generates continuous wave (CW) radiation in a range of about 1 THz to about 10 THz.

14. The imaging system of claim 12, wherein said quantum cascade laser generates CW radiation having at least one frequency component in a range of about 2 THz to about 5 THz.

15. The imaging system of claim 13, wherein said quantum cascade laser generates said terahertz radiation at a power greater than about 1 mW.

16. The imaging system of claim 15, wherein said quantum cascade laser generates said terahertz radiation at a power level in a range of about 1 mW to about 10 mW.

17. A terahertz imaging system, comprising
a source of terahertz radiation generating radiation pulses having one or more frequency components in a range of about 1 THz to about 10 THz,
an optical system for directing said radiation pulses to an object to be imaged,
a two-dimensional array of airbridge bolometer detecting elements for detecting at least a portion of the THz radiation transmitted through the object or reflected by the object, said detecting elements having temperature sensitive elements adapted to absorb said transmitted or reflected THz radiation and convert said absorbed radiation into heat to generate detection signals, said elements being further adapted to generate reference signals corresponding to detection of ambient infrared radiation in absence of said THz radiation, wherein a number of said detecting elements in at least one of said dimensions is greater than about 120,
a processor in communication with said detector array,
wherein said processor generates a THz image of the object based on a difference of said detection and reference signals, and
wherein no antenna is utilized in said bolometer detecting elements.

18. The terahertz imaging system of claim 17, wherein said array of detecting elements generate said detection and reference signals during at least two different temporal periods.

19. The terahertz imaging system of claim 17, wherein said source is configured to generate a radiation pulse during the temporal period in which said detection signals are generated.

20. The terahertz imaging system of claim 19, wherein said radiation pulse has a duration less than that of the temporal period in which the detection signals are generated.

21. The terahertz imaging system of claim 17, wherein said radiation source comprises a quantum cascade laser.

22. The terahertz imaging system of claim 17, wherein said imaging system generates images of the object at a rate of in a range of about 20 to 60 images per second.

23. The terahertz imaging system of claim 17, wherein said detecting elements comprise uncooled bolometer detecting elements.

24. A terahertz imaging system, comprising:
a plurality of terahertz radiation sources for generating radiation at different frequencies in a range of about 1 THz to about 10 THz,
an optical system for directing radiation from said sources to an object to be imaged,
a controller in communication with said sources for selectively activating the sources to illuminate the object at different frequencies,
a two-dimensional array of radiation detecting elements each having a temperature sensitive element adapted to absorb at least a portion of radiation transmitted through said object or reflected by the object and convert said absorbed radiation into heat to generate at least two images of the object corresponding to two of said frequencies,
wherein a number of said radiation detecting elements in at least one of said dimensions is greater than about 120, and
wherein no antenna is utilized in said radiation detecting elements.

25. The terahertz imaging system of claim 24, wherein said radiation sources comprise quantum cascade lasers.

26. The terahertz imaging system of claim 24, wherein said radiation detecting elements comprise bolometer detection elements.

27. A terahertz imaging system, comprising
a source for generating radiation having one or more frequency components in a range of about 5 THz to about 10 THz,
an optical system for directing said radiation to an object to be imaged,
a two-dimensional array of bolometer radiation detecting elements disposed relative to said object to receive at least a portion of the radiation transmitted through the object or reflected by the object, said detecting elements having temperature sensitive elements adapted to absorb at least a portion of said transmitted or reflected radiation and convert said absorbed radiation into heat so as to detect said transmitted or reflected radiation and to form a terahertz image of said object,
wherein a number of said radiation detecting elements in at least one of said dimensions is greater than about 120, and
wherein no antenna is utilized in said bolometer radiation detecting elements.

28. The terahertz imaging system of claim 27, wherein said radiation source comprises a QCL.

29. The terahertz imaging system of claim 27, wherein said detector array comprises an array of microbolometer elements.

30. A method of terahertz imaging, comprising
acquiring two or more terahertz images at one or more frequencies in a range of about 1 THz to about 10 THz of a material disposed within a visibly opaque container using a two-dimensional array of bolometer detector elements adapted to receive THz radiation on a temperature sensitive element thereof, said bolometer detector elements absorbing the received THz radiation and converting said absorbed radiation into heat, wherein a number of said bolometer detector elements in at least one of said dimensions is greater than about 120 and wherein no antenna is utilized in said bolometer detector elements, and
identifying said material by comparing said images with known terahertz spectral signatures of said material.

31. The terahertz imaging system of claim 1, wherein the source is configured for generating radiation in a range of about 5 THz to about 10 THz.

32. The terahertz imaging system of claim 1, wherein the number of said detector elements in at least one of said dimensions is greater than about 160.

33. The terahertz imaging system of claim 27, wherein said microbolometer elements comprise airbridge microbolometer elements.

34. A terahertz imaging system, comprising
at least two terahertz radiation sources for generating radiation at different frequencies in a range of about 1 THz to about 10 THz,
a two-dimensional airbridge bolometer detector array for detecting radiation generated by the at least two radiation sources, and
an optical system for directing radiation from the at least two sources to the airbridge bolometer detector array,
wherein the bolometer detectors of the array comprise temperature sensitive elements adapted to absorb the terahertz radiation and convert said absorbed radiation into heat, thereby detecting the radiation, wherein a number of said temperature sensitive elements in at least one of said dimensions is greater than about 120, and wherein no antenna is utilized in said airbridge bolometer detector array.

35. The terahertz imaging system of claim 34, wherein the number of temperature sensitive elements in at least one of the dimensions is greater than about 160.

36. A terahertz imaging system, comprising a source of terahertz radiation for generating radiation pulses having one or more frequency components in a range of about 1 THz to about 10 THz, an optical system for directing said radiation pulses to an object to be imaged, a two-dimensional array of airbridge bolometer detecting elements for absorbing at least a portion of the THz radiation transmitted through the object or reflected by the object and converting said absorbed radiation into heat to generate detection signals, each of said bolometer elements having a temperature sensitive element configured to receive said THz radiation and to be heated thereby, and a read-out element electrically coupled to the sensing element to detect a change in temperature of the sensing element, wherein a number of said bolometer detecting elements in at least one of said dimensions is greater than about 120 and wherein no antenna is utilized in said bolometer detecting elements, a processor in communication with said detector array, wherein said processor generates a THz image of the object based on said detection signals.

* * * * *